United States Patent
Xu et al.

(10) Patent No.: US 6,387,681 B1
(45) Date of Patent: *May 14, 2002

(54) **METHOD FOR CLONING AND EXPRESSION OF NHEI RESTRICTION ENDONUCLEASE IN *E. COLI*.**

(75) Inventors: Shuang-yong Xu, Lexington; Jian-ping Xiao, Wenham, both of MA (US)

(73) Assignee: New England Biolabs, Inc., Beverly, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/428,747

(22) Filed: Oct. 28, 1999

(51) Int. Cl.$^7$ ............................ C12N 9/22; C12N 15/55
(52) U.S. Cl. ................. 435/199; 435/252.3; 435/320.1; 536/23.2
(58) Field of Search ................................ 530/820, 875, 530/806, 350, 300; 536/23.2, 23.7; 435/69.1, 71.1, 69.3, 199, 320.1, 252.3; 935/11, 14; 424/94.1

(56) References Cited

U.S. PATENT DOCUMENTS

| 5,200,333 A | 4/1993 | Wilson et al. ............ 435/172.3 |
| 5,476,768 A | * 12/1995 | Pearson et al. ................. 435/6 |
| 5,498,535 A | 3/1996 | Fomenkov et al. ....... 435/172.3 |

FOREIGN PATENT DOCUMENTS

| WO | WO 99/11821 | 3/1998 |
| WO | WO 99/64632 | 12/1999 |

OTHER PUBLICATIONS

Kosykh, et al., Mol. Gen. Genet. 178:717–719 (1980).
Mann, et al., Gene 3:97–112 (1978).
Walder, et al., Proc. Nat. Acad. Sci. USA 78:1503–1507 (1981).
Bougueleret, et al., Nucl. Acids Res. 12:3659–3676 (1984).
Gingeras and Brooks, Proc. Natl. Acad. Sci. USA 80:402–406 (1983).
Theriault and Roy, Gene 19:355–359 (1982).
Blumenthal, et al., J. Bacteriol. 164:501–509 (1985).
Wayne, et al., Gene 202:83–88 (1997).
Kiss, et al., Nucl. Acids Res. 13:6403–6421 (1985).
Szomolanyi, et al., Gene 10:219–225 (1980).
Janulaitis, et al., Gene 20:197–204 (1982).
Kiss and Baldauf, Gene 21:111–119 (1983).
Walder, et al., J. Biol. Chem. 258:1235–1241 (1983).
Fomenkov, et al., Nucl. Acids Res. 22:2399–2403 (1994).
Skoglund, et al., Gene 88:1–5 (1990).

* cited by examiner

*Primary Examiner*—Charles L. Patterson, Jr.
(74) *Attorney, Agent, or Firm*—Gregory D. Williams

(57) ABSTRACT

The present invention relates to recombinant DNA which encodes the NheI restriction endonuclease as well as NheI methyltransferase, expression of NheI restriction endonuclease from *E. coli* cells containing the recombinant DNA. An internal NdeI site in the nheIR gene was eliminated by a silent mutation. A new NdeI site was engineered at the start codon of nheIR gene. An NdeI-BamHI fragment containing nheIR gene was cloned into a T7 expression vector pAII17 and expressed in a premodified host ER2566 [pACYC-NheIM, pAII17-NheIR2]. The recombinant clone produces approximately 10 million units of NheI per gram of wet cells.

6 Claims, 5 Drawing Sheets

FIG. 2

```
    ATGAAATTATGGAATATTATTAATGATGATGCTGTGTCTGGACTTAAAAAGTTAGAAGAC
1   ------------+---------+---------+---------+---------+---------+   60
    M  K  L  W  N  I  I  N  D  D  A  V  S  G  L  K  K  L  E  D
    TCATCAATCCAATTAACAATCACAAGCCCACCATATTATAATCTTAGAAACTATGCGTGT
61  ------------+---------+---------+---------+---------+---------+  120
    S  S  I  Q  L  T  I  T  S  P  P  Y  Y  N  L  R  N  Y  A  C
    GGTGAATCAGAAATTGGGAAGGAGAGTAGTATTAATGAGTATATAAATAAATTGCAAGAT
121 ------------+---------+---------+---------+---------+---------+  180
    G  E  S  E  I  G  K  E  S  S  I  N  E  Y  I  N  K  L  Q  D
    GTATTTGAAATACTTTTTAAAAAAAACCAAATCTGATGGATTGTTATTTTTGAATTTAGGT
181 ------------+---------+---------+---------+---------+---------+  240
    V  F  E  I  L  F  K  K  T  K  S  D  G  L  L  F  L  N  L  G
    GATAGTTATATAAACGGAGAATTAGCTGGTATTCCTTGGCGTGTAGCGCTTTCATTAAAA
241 ------------+---------+---------+---------+---------+---------+  300
    D  S  Y  I  N  G  E  L  A  G  I  P  W  R  V  A  L  S  L  K
    GAATTAGGTTGGATATTACGTTCTGATATTATTTGGCATAAACCTAATGCAATGCCCTCA
301 ------------+---------+---------+---------+---------+---------+  360
    E  L  G  W  I  L  R  S  D  I  I  W  H  K  P  N  A  M  P  S
    TCAGTAAAAAATAGACCTACAGTAGACCATGAATATATATTTATGTTTGCAAAAAGCAAA
361 ------------+---------+---------+---------+---------+---------+  420
    S  V  K  N  R  P  T  V  D  H  E  Y  I  F  M  F  A  K  S  K
    CAATACAAATATAACCAAGATTCCATTCGTGAGCCTCATGTTACATTCAGTGAGTTATCA
421 ------------+---------+---------+---------+---------+---------+  480
    Q  Y  K  Y  N  Q  D  S  I  R  E  P  H  V  T  F  S  E  L  S
    AAAATGCGTGGTGGTAGAAGTCATTTTGGGAAAAGGGAAGGAACACCTGAAAAAGGAAAA
481 ------------+---------+---------+---------+---------+---------+  540
    K  M  R  G  G  R  S  H  F  G  K  R  E  G  T  P  E  K  G  K
    AATGAAGGAAATAAAAATCTTCATGATGGAAGATGGGATCAGGCATTTCATCCCCAAGGA
541 ------------+---------+---------+---------+---------+---------+  600
    N  E  G  N  K  N  L  H  D  G  R  W  D  Q  A  F  H  P  Q  G
    AGAAATAAACGTACAGTATGGAGTATCTCTTTAGGAAAATTCCGAGGCACTCACTTTGCA
601 ------------+---------+---------+---------+---------+---------+  660
    R  N  K  R  T  V  W  S  I  S  L  G  K  F  R  G  T  H  F  A
    GTTTTTCCTGAGAAATTAGTTGAAGTTTGCGTGAAGGCTGGATCGGATCCAAATGATTTA
661 ------------+---------+---------+---------+---------+---------+  720
    V  F  P  E  K  L  V  E  V  C  V  K  A  G  S  D  P  N  D  L
    ATTTGTGATCCATTTTCAGGATCTGCAACAACAGGAGTAGTTGCAATACGATTAAATCGT
721 ------------+---------+---------+---------+---------+---------+  780
    I  C  D  P  F  S  G  S  A  T  T  G  V  V  A  I  R  L  N  R
    CGTTTCATTGGTATAGAACTTTCTGAAAATTATTGTCAACTTGCAGAAGATCGTTTGAAA
781 ------------+---------+---------+---------+---------+---------+  840
    R  F  I  G  I  E  L  S  E  N  Y  C  Q  L  A  E  D  R  L  K
    TCGGAAGTGCCGAATTTAGCAAGCCGTAGCCTGCATACCTAG
841 ------------+---------+---------+---          882
    S  E  V  P  N  L  A  S  R  S  L  H  T  *
```

FIG. 3

```
    ATGAGTTCTTATCATGATGATTTAAATATATTGAACGTTGATTTTAATCATTTACGACTA
1   ------------+---------+---------+---------+---------+---------+   60
    M  S  S  Y  H  D  D  L  N  I  L  N  V  D  F  N  H  L  R  L
    ACAGAATTGATTAAACTTGCTGATCAAGCAGAGCCTTTCTATTTATGGGTAGAAAAAATA
61  ------------+---------+---------+---------+---------+---------+   120
    T  E  L  I  K  L  A  D  Q  A  E  P  F  Y  L  W  V  E  K  I
    TTTCGACAAGTCTCAGGCCGCGCAGATTCACTTGAAACTATTATTGAAGTTGAAGAGCGA
121 ------------+---------+---------+---------+---------+---------+   180
    F  R  Q  V  S  G  R  A  D  S  L  E  T  I  I  E  V  E  E  R
    GTTGTACTTAAAATGGCAATTCTTACTTGTTTTACTTCAGACGAAAAAGAATTACCAAAA
181 ------------+---------+---------+---------+---------+---------+   240
    V  V  L  K  M  A  I  L  T  C  F  T  S  D  E  K  E  L  P  K
    CTATTTAATGGAGTAGGAGTACCTTATCCGCATATTAAAGCATGTTATTTTTTCTTTGCA
241 ------------+---------+---------+---------+---------+---------+   300
    L  F  N  G  V  G  V  P  Y  P  H  I  K  A  C  Y  F  F  F  A
    TGGCTTGTTAGAGATGCTGCTACACAAAGATTAGATCCTCTAATTCGTGAAGCATTTACT
301 ------------+---------+---------+---------+---------+---------+   360
    W  L  V  R  D  A  A  T  Q  R  L  D  P  L  I  R  E  A  F  T
    CAGCTAAAAAGTATTCACCCTCAAATGAAGAAAACAGAGCTTGAATCGGAAATTTTTTCT
361 ------------+---------+---------+---------+---------+---------+   420
    Q  L  K  S  I  H  P  Q  M  K  K  T  E  L  E  S  E  I  F  S
    CAATTATTAGTCAATTATAGAAATGAATTAATACATTTTTCATGGCCTGTGATCCGAGAG
421 ------------+---------+---------+---------+---------+---------+   480
    Q  L  L  V  N  Y  R  N  E  L  I  H  F  S  W  P  V  I  R  E
    GTACTTATTTCTAGATTAGAAGGCTCGCGAAGAGCAGCAAGGGGAAGTTATCTTGAATTA
481 ------------+---------+---------+---------+---------+---------+   540
    V  L  I  S  R  L  E  G  S  R  R  A  A  R  G  S  Y  L  E  L
    TTTGTGAGAACAGCATTGGCACAGAGTATTACTTATTTTTATAAAATATATGGTAACTAT
541 ------------+---------+---------+---------+---------+---------+   600
    F  V  R  T  A  L  A  Q  S  I  T  Y  F  Y  K  I  Y  G  N  Y
    GGGAAATTCCTTGATGTGAAAATTCACGATAAACCATTAAAGGTGAAAAATAGAACATAT
601 ------------+---------+---------+---------+---------+---------+   660
    G  K  F  L  D  V  K  I  H  D  K  P  L  K  V  K  N  R  T  Y
    GATGTTGTAGCTGAATTAATTGGAAATAATCACAATACCCAATATTTGATTCTTCCAGTT
661 ------------+---------+---------+---------+---------+---------+   720
    D  V  V  A  E  L  I  G  N  N  H  N  T  Q  Y  L  I  L  P  V
    AAAACTCGTGAGACTCAAGGTGGGGGGCATGCTCATCTTTTTACTCGTGATATTGAGCAA
721 ------------+---------+---------+---------+---------+---------+   780
    K  T  R  E  T  Q  G  G  G  H  A  H  L  F  T  R  D  I  E  Q
    TCAAATAATGATATTCGAGAACTTTATCCAAACGCAGTGATTGCTCCCGTCATAATTGCA
781 ------------+---------+---------+---------+---------+---------+   840
    S  N  N  D  I  R  E  L  Y  P  N  A  V  I  A  P  V  I  I  A
    GAAAACTGGTCAGATACCGAAAAAGATTTAGAAAATGTTGGTTACAATGATATTTTTCAT
841 ------------+---------+---------+---------+---------+---------+   900
    E  N  W  S  D  T  E  K  D  L  E  N  V  G  Y  N  D  I  F  H
    TTTTCAGTAAACCCAAATAGATTTGCTGGATTTTCTGATGTAGAACAGATTAGGCTTAAT
901 ------------+---------+---------+---------+---------+---------+   960
    F  S  V  N  P  N  R  F  A  G  F  S  D  V  E  Q  I  R  L  N
    AGGTTGGTAGAAAGGATTTTATTATGA
961 ------------+---------+-------  987
    R  L  V  E  R  I  L  L  *
``` x INDICATES THE SILENT MUTATION INTRODUCED IN nheIR GENE TO ELIMINATE THE INTERNAL NdeI SITE.

SEQUENCE LISTING

<160> NUMBER OF SEQ ID NOS: 16

<210> SEQ ID NO 1
<211> LENGTH: 882
<212> TYPE: DNA
<213> ORGANISM: Neisseria mucosa heidelbergensis
<220> FEATURE:
<221> NAME/KEY: CDS
<222> LOCATION: (1)..(879)

<400> SEQUENCE: 1

```
atg aaa tta tgg aat att att aat gat gat g ct gtg tct gga ctt aaa        48
Met Lys Leu Trp Asn Ile Ile Asn Asp Asp A la Val Ser Gly Leu Lys
 1               5                  10                  15 aag tta gaa gac tca tca atc caa tta aca a tc aca agc cca cca tat        96
Lys Leu Glu Asp Ser Ser Ile Gln Leu Thr I le Thr Ser Pro Pro Tyr
             20                  25                  30 tat aat ctt aga aac tat gcg tgt ggt gaa t ca gaa att ggg aag gag       144
Tyr Asn Leu Arg Asn Tyr Ala Cys Gly Glu S er Glu Ile Gly Lys Glu
         35                  40                  45 agt agt att aat gag tat ata aat aaa ttg c aa gat gta ttt gaa ata       192
Ser Ser Ile Asn Glu Tyr Ile Asn Lys Leu G ln Asp Val Phe Glu Ile
     50                  55                  60 ctt ttt aaa aaa acc aaa tct gat gga ttg t ta ttt ttg aat tta ggt       240
Leu Phe Lys Lys Thr Lys Ser Asp Gly Leu L eu Phe Leu Asn Leu Gly
 65                  70                  75                  80 gat agt tat ata aac gga gaa tta gct ggt a tt cct tgg cgt gta gcg       288
Asp Ser Tyr Ile Asn Gly Glu Leu Ala Gly I le Pro Trp Arg Val Ala
                 85                  90                  95 ctt tca tta aaa gaa tta ggt tgg ata tta c gt tct gat att att tgg       336
Leu Ser Leu Lys Glu Leu Gly Trp Ile Leu A rg Ser Asp Ile Ile Trp
            100                 105                 110 cat aaa cct aat gca atg ccc tca tca gta a aa aat aga cct aca gta       384
His Lys Pro Asn Ala Met Pro Ser Ser Val L ys Asn Arg Pro Thr Val
        115                 120                 125 gac cat gaa tat ata ttt atg ttt gca aaa a gc aaa caa tac aaa tat       432
Asp His Glu Tyr Ile Phe Met Phe Ala Lys S er Lys Gln Tyr Lys Tyr
    130                 135                 140 aac caa gat tcc att cgt gag cct cat gtt a ca ttc agt gag tta tca       480
Asn Gln Asp Ser Ile Arg Glu Pro His Val T hr Phe Ser Glu Leu Ser
145                 150                 155                 160 aaa atg cgt ggt ggt aga agt cat ttt ggg a aa agg gaa gga aca cct       528
Lys Met Arg Gly Gly Arg Ser His Phe Gly L ys Arg Glu Gly Thr Pro
                165                 170                 175 gaa aaa gga aaa aat gaa gga aat aaa aat c tt cat gat gga aga tgg       576
Glu Lys Gly Lys Asn Glu Gly Asn Lys Asn L eu His Asp Gly Arg Trp
            180                 185                 190 gat cag gca ttt cat ccc caa gga aga aat a aa cgt aca gta tgg agt       624
Asp Gln Ala Phe His Pro Gln Gly Arg Asn L ys Arg Thr Val Trp Ser
        195                 200                 205 atc tct tta gga aaa ttc cga ggc act cac t tt gca gtt ttt cct gag       672
Ile Ser Leu Gly Lys Phe Arg Gly Thr His P he Ala Val Phe Pro Glu
    210                 215                 220 aaa tta gtt gaa gtt tgc gtg aag gct gga t cg gat cca aat gat tta       720
```

```
Lys Leu Val Glu Val Cys Val Lys Ala Gly Ser Asp Pro Asn Asp Leu
225                 230                 235                 240 att tgt gat cca ttt tca gga tct gca aca a ca gga gta gtt gca ata         768
Ile Cys Asp Pro Phe Ser Gly Ser Ala Thr Thr Gly Val Val Ala Ile
                245                 250                 255 cga tta aat cgt cgt ttc att ggt ata gaa c tt tct gaa aat tat tgt         816
Arg Leu Asn Arg Arg Phe Ile Gly Ile Glu Leu Ser Glu Asn Tyr Cys
                260                 265                 270 caa ctt gca gaa gat cgt ttg aaa tcg gaa g tg ccg aat tta gca agc         864
Gln Leu Ala Glu Asp Arg Leu Lys Ser Glu Val Pro Asn Leu Ala Ser
                275                 280             285 cgt agc ctg cat acc tag                                                  882
Arg Ser Leu His Thr
        290
```

<210> SEQ ID NO 2
<211> LENGTH: 293
<212> TYPE: PRT
<213> ORGANISM: Neisseria mucosa heidelbergensis

<400> SEQUENCE: 2

```
Met Lys Leu Trp Asn Ile Ile Asn Asp Asp Ala Val Ser Gly Leu Lys
  1               5                  10                  15

Lys Leu Glu Asp Ser Ser Ile Gln Leu Thr Ile Thr Ser Pro Pro Tyr
                 20                  25                  30

Tyr Asn Leu Arg Asn Tyr Ala Cys Gly Glu Ser Glu Ile Gly Lys Glu
             35                  40                  45

Ser Ser Ile Asn Glu Tyr Ile Asn Lys Leu Gln Asp Val Phe Glu Ile
         50                  55                  60

Leu Phe Lys Lys Thr Lys Ser Asp Gly Leu Leu Phe Leu Asn Leu Gly
 65                  70                  75                  80

Asp Ser Tyr Ile Asn Gly Glu Leu Ala Gly Ile Pro Trp Arg Val Ala
                 85                  90                  95

Leu Ser Leu Lys Glu Leu Gly Trp Ile Leu Arg Ser Asp Ile Ile Trp
                100                 105                 110

His Lys Pro Asn Ala Met Pro Ser Ser Val Lys Asn Arg Pro Thr Val
            115                 120                 125

Asp His Glu Tyr Ile Phe Met Phe Ala Lys Ser Lys Gln Tyr Lys Tyr
        130                 135                 140

Asn Gln Asp Ser Ile Arg Glu Pro His Val Thr Phe Ser Glu Leu Ser
145                 150                 155                 160

Lys Met Arg Gly Gly Arg Ser His Phe Gly Lys Arg Glu Gly Thr Pro
                165                 170                 175

Glu Lys Gly Lys Asn Glu Gly Asn Lys Asn Leu His Asp Gly Arg Trp
            180                 185                 190

Asp Gln Ala Phe His Pro Gln Gly Arg Asn Lys Arg Thr Val Trp Ser
        195                 200                 205

Ile Ser Leu Gly Lys Phe Arg Gly Thr His Phe Ala Val Phe Pro Glu
    210                 215                 220

Lys Leu Val Glu Val Cys Val Lys Ala Gly Ser Asp Pro Asn Asp Leu
225                 230                 235                 240

Ile Cys Asp Pro Phe Ser Gly Ser Ala Thr Thr Gly Val Val Ala Ile
                245                 250                 255

Arg Leu Asn Arg Arg Phe Ile Gly Ile Glu Leu Ser Glu Asn Tyr Cys
            260                 265                 270

Gln Leu Ala Glu Asp Arg Leu Lys Ser Glu Val Pro Asn Leu Ala Ser
```

275                 280                 285
Arg Ser Leu His Thr
        290

<210> SEQ ID NO 3
<211> LENGTH: 987
<212> TYPE: DNA
<213> ORGANISM: Neisseria mucosa heidelbergensis
<220> FEATURE:
<221> NAME/KEY: CDS
<222> LOCATION: (1)..(984)

<400> SEQUENCE: 3

| atg agt tct tat cat gat gat tta aat ata t tg aac gtt gat ttt aat | 48 |
|---|---|
| Met Ser Ser Tyr His Asp Asp Leu Asn Ile L eu Asn Val Asp Phe Asn | |
| 1               5                  10                  15 | |
| cat tta cga cta aca gaa ttg att aaa ctt g ct gat caa gca gag cct | 96 |
| His Leu Arg Leu Thr Glu Leu Ile Lys Leu A la Asp Gln Ala Glu Pro | |
|         20                  25                  30 | |
| ttc tat tta tgg gta gaa aaa ata ttt cga c aa gtc tca ggc cgc gca | 144 |
| Phe Tyr Leu Trp Val Glu Lys Ile Phe Arg G ln Val Ser Gly Arg Ala | |
|     35                  40                  45 | |
| gat tca ctt gaa act att att gaa gtt gaa g ag cga gtt gta ctt aaa | 192 |
| Asp Ser Leu Glu Thr Ile Ile Glu Val Glu G lu Arg Val Val Leu Lys | |
| 50                  55                  60 | |
| atg gca att ctt act tgt ttt act tca gac g aa aaa gaa tta cca aaa | 240 |
| Met Ala Ile Leu Thr Cys Phe Thr Ser Asp G lu Lys Glu Leu Pro Lys | |
| 65                  70                  75                  80 | |
| cta ttt aat gga gta gga gta cct tat ccg c at att aaa gca tgt tat | 288 |
| Leu Phe Asn Gly Val Gly Val Pro Tyr Pro H is Ile Lys Ala Cys Tyr | |
|             85                  90                  95 | |
| ttt ttc ttt gca tgg ctt gtt aga gat gct g ct aca caa aga tta gat | 336 |
| Phe Phe Phe Ala Trp Leu Val Arg Asp Ala A la Thr Gln Arg Leu Asp | |
|         100                 105                 110 | |
| cct cta att cgt gaa gca ttt act cag cta a aa agt att cac cct caa | 384 |
| Pro Leu Ile Arg Glu Ala Phe Thr Gln Leu L ys Ser Ile His Pro Gln | |
|     115                 120                 125 | |
| atg aag aaa aca gag ctt gaa tcg gaa att t tt tct caa tta tta gtc | 432 |
| Met Lys Lys Thr Glu Leu Glu Ser Glu Ile P he Ser Gln Leu Leu Val | |
| 130                 135                 140 | |
| aat tat aga aat gaa tta ata cat ttt tca t gg cct gtg atc cga gag | 480 |
| Asn Tyr Arg Asn Glu Leu Ile His Phe Ser T rp Pro Val Ile Arg Glu | |
| 145                 150                 155                 160 | |
| gta ctt att tct aga tta gaa ggc tcg cga a ga gca gca agg gga agt | 528 |
| Val Leu Ile Ser Arg Leu Glu Gly Ser Arg A rg Ala Ala Arg Gly Ser | |
|             165                 170                 175 | |
| tat ctt gaa tta ttt gtg aga aca gca ttg g ca cag agt att act tat | 576 |
| Tyr Leu Glu Leu Phe Val Arg Thr Ala Leu A la Gln Ser Ile Thr Tyr | |
|         180                 185                 190 | |
| ttt tat aaa ata tat ggt aac tat ggg aaa t tc ctt gat gtg aaa att | 624 |
| Phe Tyr Lys Ile Tyr Gly Asn Tyr Gly Lys P he Leu Asp Val Lys Ile | |
|     195                 200                 205 | |
| cac gat aaa cca tta aag gtg aaa aat aga a ca tat gat gtt gta gct | 672 |
| His Asp Lys Pro Leu Lys Val Lys Asn Arg T hr Tyr Asp Val Val Ala | |
| 210                 215                 220 | |
| gaa tta att gga aat aat cac aat acc caa t at ttg att ctt cca gtt | 720 |
| Glu Leu Ile Gly Asn Asn His Asn Thr Gln T yr Leu Ile Leu Pro Val | |
| 225                 230                 235                 240 | |
| aaa act cgt gag act caa ggt ggg ggg cat g ct cat ctt ttt act cgt | 768 |
| Lys Thr Arg Glu Thr Gln Gly Gly Gly His A la His Leu Phe Thr Arg | |
|             245                 250                 255 | |

```
gat att gag caa tca aat aat gat att cga g aa ctt tat cca aac gca      816
Asp Ile Glu Gln Ser Asn Asn Asp Ile Arg G lu Leu Tyr Pro Asn Ala
            260                 265                 270 gtg att gct ccc gtc ata att gca gaa aac t gg tca gat acc gaa aaa      864
Val Ile Ala Pro Val Ile Ile Ala Glu Asn T rp Ser Asp Thr Glu Lys
            275                 280                 285 gat tta gaa aat gtt ggt tac aat gat att t tt cat ttt tca gta aac      912
Asp Leu Glu Asn Val Gly Tyr Asn Asp Ile P he His Phe Ser Val Asn
            290                 295                 300 cca aat aga ttt gct gga ttt tct gat gta g aa cag att agg ctt aat      960
Pro Asn Arg Phe Ala Gly Phe Ser Asp Val G lu Gln Ile Arg Leu Asn
305                 310                 315                 320 agg ttg gta gaa agg att tta tta tga                                   987
Arg Leu Val Glu Arg Ile Leu Leu
                325

<210> SEQ ID NO 4
<211> LENGTH: 328
<212> TYPE: PRT
<213> ORGANISM: Neisseria mucosa heidelbergensis

<400> SEQUENCE: 4

Met Ser Ser Tyr His Asp Asp Leu Asn Ile L eu Asn Val Asp Phe Asn
  1               5                  10                  15

His Leu Arg Leu Thr Glu Leu Ile Lys Leu A la Asp Gln Ala Glu Pro
             20                  25                  30

Phe Tyr Leu Trp Val Glu Lys Ile Phe Arg G ln Val Ser Gly Arg Ala
         35                  40                  45

Asp Ser Leu Glu Thr Ile Ile Glu Val Glu G lu Arg Val Val Leu Lys
     50                  55                  60

Met Ala Ile Leu Thr Cys Phe Thr Ser Asp G lu Lys Glu Leu Pro Lys
 65                  70                  75                  80

Leu Phe Asn Gly Val Gly Val Pro Tyr Pro H is Ile Lys Ala Cys Tyr
                 85                  90                  95

Phe Phe Phe Ala Trp Leu Val Arg Asp Ala A la Thr Gln Arg Leu Asp
            100                 105                 110

Pro Leu Ile Arg Glu Ala Phe Thr Gln Leu L ys Ser Ile His Pro Gln
        115                 120                 125

Met Lys Lys Thr Glu Leu Glu Ser Glu Ile P he Ser Gln Leu Leu Val
    130                 135                 140

Asn Tyr Arg Asn Glu Leu Ile His Phe Ser T rp Pro Val Ile Arg Glu
145                 150                 155                 160

Val Leu Ile Ser Arg Leu Glu Gly Ser Arg A rg Ala Ala Arg Gly Ser
                165                 170                 175

Tyr Leu Glu Leu Phe Val Arg Thr Ala Leu A la Gln Ser Ile Thr Tyr
            180                 185                 190

Phe Tyr Lys Ile Tyr Gly Asn Tyr Gly Lys P he Leu Asp Val Lys Ile
        195                 200                 205

His Asp Lys Pro Leu Lys Val Lys Asn Arg T hr Tyr Asp Val Val Ala
    210                 215                 220

Glu Leu Ile Gly Asn Asn His Asn Thr Gln T yr Leu Ile Leu Pro Val
225                 230                 235                 240

Lys Thr Arg Glu Thr Gln Gly Gly Gly His A la His Leu Phe Thr Arg
                245                 250                 255

Asp Ile Glu Gln Ser Asn Asn Asp Ile Arg G lu Leu Tyr Pro Asn Ala
            260                 265                 270
```

Val Ile Ala Pro Val Ile Ile Ala Glu Asn Trp Ser Asp Thr Glu Lys
            275                 280                 285

Asp Leu Glu Asn Val Gly Tyr Asn Asp Ile Phe His Phe Ser Val Asn
        290                 295                 300

Pro Asn Arg Phe Ala Gly Phe Ser Asp Val Glu Gln Ile Arg Leu Asn
305                 310                 315                 320

Arg Leu Val Glu Arg Ile Leu Leu
                325

<210> SEQ ID NO 5
<211> LENGTH: 24
<212> TYPE: DNA
<213> ORGANISM: Synthetic DNA

<400> SEQUENCE: 5
gaaaaataga acatatgatg ttgt                                              24

<210> SEQ ID NO 6
<211> LENGTH: 24
<212> TYPE: DNA
<213> ORGANISM: Synthetic DNA

<400> SEQUENCE: 6
acctttaatg gtttatcgtg aatt                                              24

<210> SEQ ID NO 7
<211> LENGTH: 24
<212> TYPE: DNA
<213> ORGANISM: Synthetic DNA

<400> SEQUENCE: 7
tacacaaaga ttagatcctc taat                                              24

<210> SEQ ID NO 8
<211> LENGTH: 24
<212> TYPE: DNA
<213> ORGANISM: Synthetic DNA

<400> SEQUENCE: 8
gcagcatctc taacaagcca tgca                                              24

<210> SEQ ID NO 9
<211> LENGTH: 51
<212> TYPE: DNA
<213> ORGANISM: Synthetic DNA

<400> SEQUENCE: 9
gttggatccg gaggtaaata aatgaaatta tggaatatta ttaatgatga t                51

<210> SEQ ID NO 10
<211> LENGTH: 36
<212> TYPE: DNA
<213> ORGANISM: synthetic oligos

<400> SEQUENCE: 10
aacggcgcat gctcaatcaa gcaaccgcgt gcgtgc                                 36

<210> SEQ ID NO 11
<211> LENGTH: 51
<212> TYPE: DNA
<213> ORGANISM: Synthetic DNA -continued

```
<400> SEQUENCE: 11
cgcggatccg gaggttaaaa aatgagttct tatcatgatg atttaaatat a        51

<210> SEQ ID NO 12
<211> LENGTH: 36
<212> TYPE: DNA
<213> ORGANISM: Synthetic DNA

<400> SEQUENCE: 12
tccggatcct cataataaaa tcctttctac caacct                          36

<210> SEQ ID NO 13
<211> LENGTH: 39
<212> TYPE: DNA
<213> ORGANISM: Synthetic DNA

<400> SEQUENCE: 13
tatgaggttc atatgagttc ttatcatgat gatttaaat                       39

<210> SEQ ID NO 14
<211> LENGTH: 27
<212> TYPE: DNA
<213> ORGANISM: Synthetic DNA

<400> SEQUENCE: 14
ttcagctaca acatcgtatg ttctatt                                    27

<210> SEQ ID NO 15
<211> LENGTH: 27
<212> TYPE: DNA
<213> ORGANISM: Synthetic DNA

<400> SEQUENCE: 15
aatagaacat acgatgttgt agctgaa                                    27

<210> SEQ ID NO 16
<211> LENGTH: 36
<212> TYPE: DNA
<213> ORGANISM: Synthetic DNA

<400> SEQUENCE: 16
tccggatcct cataataaaa tcctttctac caacct                          36
```

US 6,387,681 B1

METHOD FOR CLONING AND EXPRESSION OF NHEI RESTRICTION ENDONUCLEASE IN *E. COLI*.

BACKGROUND OF THE INVENTION

The present invention relates to recombinant DNA which encodes the NheI restriction endonuclease as well as NheI methyltransferase, expression of NheI restriction endonuclease from *E. coli* cells containing the recombinant DNA.

NheI restriction endonuclease is found in the strain of *Nisseria mucosa heidelbergensis* (ATCC 25999). It cleaves double-stranded DNA G/CTAGC to generate a 4-base 5' overhanging ends.

Type II restriction endonucleases are a class of enzymes that occur naturally in bacteria and in some viruses. When they are purified away from other bacterial proteins, restriction endonucleases can be used in the laboratory to cleave DNA molecules into small fragments for molecular cloning and gene characterization.

Restriction endonucleases act by recognizing and binding to particular sequences of nucleotides (the 'recognition sequence') along the DNA molecule. Once bound, they cleave the molecule within, to one side of, or to both sides of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313, (1999)).

Restriction endonucleases typically are named according to the bacteria from which they are derived. Thus, the species *Deinococcus radiophilus* for example, produces three different restriction endonucleases, named DraI, DraII and DraIII. These enzymes recognize and cleave the sequences 5'TTT/AAA3', 5'PuG/GNCCPy3' and 5'CACNNN/GTG3' respectively. *Escherichia coli* RY13, on the other hand, produces only one enzyme, EcoRI, which recognizes the sequence 5'G/AATTC3'.

A second component of bacterial restriction-modification (R-M) systems are the methyltransferase (methylases). These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of recombinant DNA technology, it is now possible to clone genes and overproduce the enzymes in large quantities. The key to isolating clones of restriction endonuclease genes is to develop a simple and reliable method to identify such clones within complex genomic DNA libraries, i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

A large number of type II restriction-modification systems have been cloned. The first cloned systems used bacteriophage infection as a means of identifying or selecting restriction endonuclease clones (EcoRII: Kosykh et al., Mol. Gen. Genet. 178: 717–719, (1980); HhaII: Mann et al., Gene 3: 97–112, (1978); PstI: Walder et al., Proc. Nat. Acad. Sci. 78: 1503–1507, (1981)). Since the presence of restriction-modification systems in bacteria enable them to resist infection by bacteriophage, cells that carry cloned restriction-modification genes can, in principle, be selectively isolated as survivors from genomic DNA libraries that have been exposed to phages. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., Nucl. Acids. Res. 12: 3659–3676, (1984); PaeR7: Gingeras and Brooks, Proc. Natl. Acad. Sci. USA 80: 402–406, (1983); Theriault and Roy, Gene 19: 355–359 (1982); PvuII: Blumenthal et al., J. Bacteriol. 164: 501–509, (1985); Tsp45I: Wayne et al. Gene 202:83–88, (1997)).

A third approach is to select for active expression of methylase genes (methylase selection) PCT/US98/18124, filed Sep. 01, 1998; PCT/US99/13295, filed Jun. 11, 1999; U.S. Pat. No. 5,200,333, issued Apr. 6, 1993 and BsuRI: Kiss et al., Nucl. Acids. Res. 13: 6403–6421, (1985)). Since R-M genes are often closely linked together, both genes can often be cloned simultaneously. This selection does not always yield a complete restriction system however, but instead yields only the methylase gene (BspRI: Szomolanyi et al., Gene 10: 219–225, (1980); BcnI: Janulaitis et al., Gene 20: 197–204 (1982); BsuRI: Kiss and Baldauf, Gene 21: 111–119, (1983); and MspI: Walder et al., J. Biol. Chem. 258: 1235–1241, (1983)).

A more recent method, the "endo-blue method", has been described for direct cloning of restriction endonuclease genes in *E. coli* based on the indicator strain of *E. coli* containing the dinD::lacZ fusion (Fomenkov et al., U.S. Pat. No. 5,498,535, (1996); Fomenkov et al., Nucl. Acids Res. 22:2399–2403, (1994)). This method utilizes the *E. coli* SOS response following DNA damages caused by restriction endonucleases or non-specific nucleases. A number of thermostable nuclease genes (TaqI, Tth111I, BsoBI, Tf nuclease) have been cloned by this method (U.S. Pat. No. 5,498,535, (1996).

Because purified restriction endonucleases, and to a lesser extent, modification methylases, are useful tools for creating recombinant molecules in the laboratory, there is a commercial incentive to obtain bacterial strains through recombinant DNA techniques that produce large quantities of restriction enzymes. Such overexpression strains should also simplify the task of enzyme purification.

SUMMARY OF THE INVENTION

*Nisseria mucosa heidelbergensis* genomic DNA was digested partially with ApoI and genomic DNA fragments in the range of 2–10 kb were purified through a low melting agarose gel. The ApoI partial DNA fragments were ligated to EcoRI digested and CIP treated pRRS vector skolund, Gene 88:1–5 (1990). The ligated DNA was transferred into *E. coli* RR1 competent cells by electroporation. Transformants were pooled and amplified. Plasmid DNA was prepared from the cells and challenged with BfaI. BfaI recognition sequence C/TAG is the internal 4 bp of NheI recognition sequence G/CTAGC. It was reasoned that cloning and expression of NheI methylase may confer resistance to BfaI digestion. The BfaI challenged DNA was transformed into RR1 cells. Survivors were screened for resistance to NheI digestion. However, no NheI resistant clones were detected.

In order to clone the NheI methylase gene (nheIM), one NheI linker was inserted into SspI and HincII sites respectively in pRRS. The modified plasmid with two NheI sites was named pRRS10. Vector pRRS10 was digested with EcoRI, treated with CIP, and gel-purified. The ApoI partial DNA fragments were ligated to pRRS10 with compatible ends. The methylase selection method was used to clone nheIM gene. Ten resistant clones were isolated from the ApoI partial library. One resistant clone #22 contains an insert of about 2.8–3 kb. The entire insert was sequenced by primer walking. The nheIM gene is 882 bp, encoding a 293-aa protein with predicted molecular mass of 33,268 daltons.

There is one gene downstream of nheIM gene that has 43% identity to a 20 kDa hypothetical protein (O47152) of *E. coli* . There is one partial open reading frame (orf) upstream of nheIM gene that doe not show any homology to known genes in GenBank. Since restriction endonucleases usually are not homologous to each other (except among some isoschizomers), it was concluded that the upstream orf is most likely the nheIR gene. Efforts were made to obtain the upstream DNA coding sequence by inverse PCR amplification. *N. mucosa heidelbergensis* genomic DNA was digested with AluI, HaeII, HhaI, NheI, NlaIII, NspI, SphI, SspI, StyI, TaqI, and TfiI, respectively. The digested DNA was self-ligated at a low DNA concentration and then used for inverse PCR amplification of the nheIR gene. Inverse PCR products were found in AluI, NlaIII, NspI, StyI, and TaqI digested/self-ligated DNA. The inverse PCR products were gel-purified and sequenced which provided 339-bp new DNA sequence. A second round of inverse PCR was performed to amplify more of the upstream sequence. Inverse PCR products were found in ApoI, AseI, RsaI, SspI, and TaqI digested/self-ligated DNA. The PCR products were sequenced directly using PCR primers. An additional 329-bp new sequence was derived. One open reading frame of 987 bp was found upstream of nheIM gene. This orf was designated as nheIR gene, which encodes a 328-aa protein with predicted molecular mass of 38,197 daltons.

Two primers were synthesized to amplify nheIM gene in PCR. Following digestion with BamHI and SphI, the PCR product was ligated into pACYC184 with compatible ends. Plasmids with nheIM gene inserts were screened for resistance to NheI digestion. Eleven clones out of 18 were resistant to NheI digestion, indicating efficient M.NheI expression in *E. coli* cells and NheI site modification on the expression plasmid. The host cell ER2683 [pACYC-NheIM] was used for expression of nheIR gene.

The nheIR gene was amplified in PCR, digested with BamHI and ligated into pUC19lacI$^q$ or pAII17. The expression level from pUC19lacI$^q$-NheIR was approximately 10,000 units of NheI per gram of wet cells. The native NheI producing strain *N. mucosa heidelbergensis* produces about 100,000 units of NheI per gram of wet cells. So the NheI yield in the first recombinant strain is about 10-fold lower than the native strain. The second expression strain carrying pAII17-NheIR1 produces approximately 100,000 units of NheI, which is about the same level as that produced in the native strain *N. mucosa heidelbergensis*. To further improve the NheI expression level, the internal NdeI site within nheIR gene was mutagenized by introduction of a silent mutation. A new NdeI site was engineered at the beginning of the gene in the forward primer. A BamHI site was introduced in the reverse primer. The nheIR gene was amplified in PCR, digested with NdeI and BamHI and cloned into the T7 expression vector pAII17. The fusion of ATG start codon of nheIR gene to the NdeI site in the expression vector increased NheI expression level to 10 million units NheI per gram of wet *E. coli* cells. The recombinant NheI expression level in the *E. coli* overproducing strain is 100-fold higher than the native source.

BRIEF DESCRIPTION OF THE DRAWINGS

FIG. 2. DNA sequence of NheI methylase gene (SEQ ID NO:1) (nheIM) and its encoded amino acid sequence (SEQ ID NO:2).

FIG. 3. DNA sequence of NheI endonuclease gene (SEQ ID NO:3) (nheIR) and its encoded amino acid sequence (SEQ ID NO:4).

DETAILED DESCRIPTION OF THE INVENTION

Figure 1:
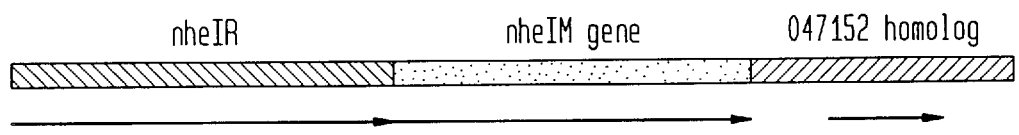
FIG. 1. Gene organization of NheI restriction-modification system. Genes nheIR and nheIM code for NheI endonuclease and NheI methylase (M.NheI), respectively. O47152 encodes a hypothetical 20 kDa protein in *E. coli*.

The method described herein by which the NheI methylase gene and the NheI restriction endonuclease genes are preferably cloned and expressed in *E. coli* using the following steps:

1. Preparation of Genomic DNA and ApoI Partial Digestion

Genomic DNA is prepared from *Neisseria mucosa heidelbergensis* (ATCC 25999) by the standard procedure. The genomic DNA was digested partially with ApoI (ApoI recognition sequence R/AATTY. Genomic DNA fragments in the range of 2–10 kb are purified through a low melting agarose gel.

2. Construction of ApoI Partial Genomic DNA Library and Challenge of Library with BfaI The ApoI partial DNA fragments are ligated to EcoRI digested and CIP treated pRRS vector. The ligated DNA is transferred into *E. coli* RR1 competent cells by electroporation. Transformants are pooled and amplified. Plasmid DNA is prepared from the cells and challenged with BfaI. BfaI recognition sequence C/TAG is the internal 4 bp of NheI recognition sequence G/CTAGC. It is reasoned that cloning and expression of NheI methylase may confer resistance to BfaI digestion. The BfaI challenged DNA is transformed into RR1 cells. Survivors are screened for resistance to NheI digestion. No NheI resistant clones are found in the library.

3. Construction of a New Cloning Vector with Two NheI Sites

To create NheI sites in the cloning vector pRRS. In order to clone NheI methylase gene (nheIM), NheI linkers are inserted into SspI and HincII sites. The resulting plasmid is called pRRS10. Plasmid pRRS10 is digested with EcoRI and treated with CIP.

4. Construction of ApoI Partial Library Using pRRS10

The gel-purified ApoI partial DNA fragments are ligated into EcoRI-digested and CIP-treated pRRS10. The ligated DNA is transferred into *E. coli* RR1 competent cells by electroporation. Transformants are pooled and amplified in 1 liter culture. Plasmid DNA library is prepared from the cells and challenged with NheI. The challenged DNA is used for transformation into RR1 cells. Transformants are cultured overnight and plasmid DNA is prepared. The plasmid DNA is digested with NheI to check any resistance. Ten isolates are found to be resistant to NheI digestion. Resistance to NheI digestion could be due to loss of NheI sites in the vector or modification of NheI sites by NheI methylase.

5. DNA Sequencing of the Resistant Clones

One resistant clone #22 contains an insert of about 2.8–3 kb. The forward and reverse primers of pUC19 are used to sequence the insert. An NheI site is found inserted in the previous HincII site, indicating the resistance is caused by methylase modification and not due to the loss of NheI site. N4 cytosine methylase motifs are also found in the amino acid sequence predicted from the DNA sequence. The entire insert is sequenced by primer walking. The nheIM gene is 882 bp, encoding a 293-aa protein with predicted molecular mass of 33,268 daltons.

6. Cloning of NheI Restriction Endonuclease Gene (nheIR)

There is one gene downstream of nheIM gene that has 43% identity to a 20 kDa hypothetical protein (O47152) of *E. coli*. Upstream of nheIM gene there is one open reading frame (orf) that does not show any homology to known genes in GenBank. Since restriction endonucleases usually are not homologous to each other (except among some isoschizomers), it is concluded that the upstream orf is most likely the nheIR gene. Efforts are made to obtain the upstream DNA coding sequence by inverse PCR amplification. *N. mucosa heidelbergensis* genomic DNA is digested with AluI, HaeII, HhaI, NheI, NlaIII, NspI, SphI, SspI, StyI, TaqI, and TfiI, respectively. The digested DNA is ligated at a low DNA concentration and then used for inverse PCR amplification of nheIR gene. Inverse PCR products are found in AluI, NlaIII, NspI, StyI, and TaqI digested/self-ligated DNA. The inverse PCR products are gel-purified and sequenced which provided 339 bp of new DNA sequence. A second round of inverse PCR is performed to amplify more of the upstream sequence. Inverse PCR products are found in ApoI, AseI, RsaI, SspI, and TaqI digested/self-ligated DNA. The PCR products are sequenced directly using PCR primers. An additional 329 bp of new sequence are derived. One open reading frame of 987 bp is found upstream of nheIM gene. This orf is designated as nheIR gene, which encodes a 328-aa protein with predicted molecular mass of 38,197 daltons.

7. Expression of nheIM Gene in *E. coli*

Two primers are synthesized to amplify nheIM gene in PCR. Following digestion with BamHI and SphI, the PCR product is ligated into pACYC184 with the compatible ends. The ligated DNA is transformed into ER2683 competent cells. Plasmids with nheIM gene inserts are tested for resistance to NheI digestion. Eleven clones out of 18 are resistant to NheI digestion, indicating efficient M.NheI expression in *E. coli* cells and NheI site modification on the expression plasmid. The host cell ER2683 [pACYC-NheIM] is used for expression of nheIR gene.

8. Expression of nheIR Gene in *E. coli* Using a High Copy Plasmid pUC19lacI$^q$ The nheIR gene is amplified in PCR, digested with BaffEI and ligated into pUC19lacI$^q$ (BamHI digested and CIP treated). After transformation of the ligated DNA into ER2683 [pACYC-NheIM], transformants are screened for the endonuclease gene insert. Four clones out of 36 contain nheIR gene insert. All four clones (#2, #11, #12, and #30) are induced with IPTG and cell extracts are prepared and assayed for NheI endonuclease activity. Clone #12 produces approximately 10,000 units of NheI per gram of wet cells. The native NheI producing strain *N. mucosa heidelbergensis* produces about 100,000 units of NheI per gram of wet cells. So the NheI yield in the recombinant strain is about 10-fold lower than the native strain.

9. Expression of nheIR Gene in a T7 Expression Vector pAII17

The T7 expression vector pAII17 uses NdeI and BamHI sites for insertion of target gene into the vector. There is a ribosome-binding site upstream of the NdeI site. The start codon (ATG) of the gene to be expressed is fused to the NdeI site (CATATG). However, there is one NdeI site within the nheIR gene so that the NdeI site cannot be used for cloning into pAII17. To solve this problem, BamHI sites are engineered in the forward and reverse primers. A ribosome binding site is also included in the forward primer. The nheIR gene is amplified in PCR, digested with BamHI and ligated to BamHI-digested and CIP treated pAII17 vector. The ligated DNA is transformed into ER2683 [pACYC-NheIM]. Three clones out of 36 contain the nheIR gene insert. Cells ER2683 [pACYC-NheIM, pAII17-NheIR1] are induced with IPTG and cell extracts are prepared and assayed for NheI activity. The T7 expression strain produces approximately 100,000 units of NheI, which is about the same level as that produced in the native strain *N. mucosa heidelbergensis*. Further overexpression work is needed to improve the NheI yield.

Figure 4:
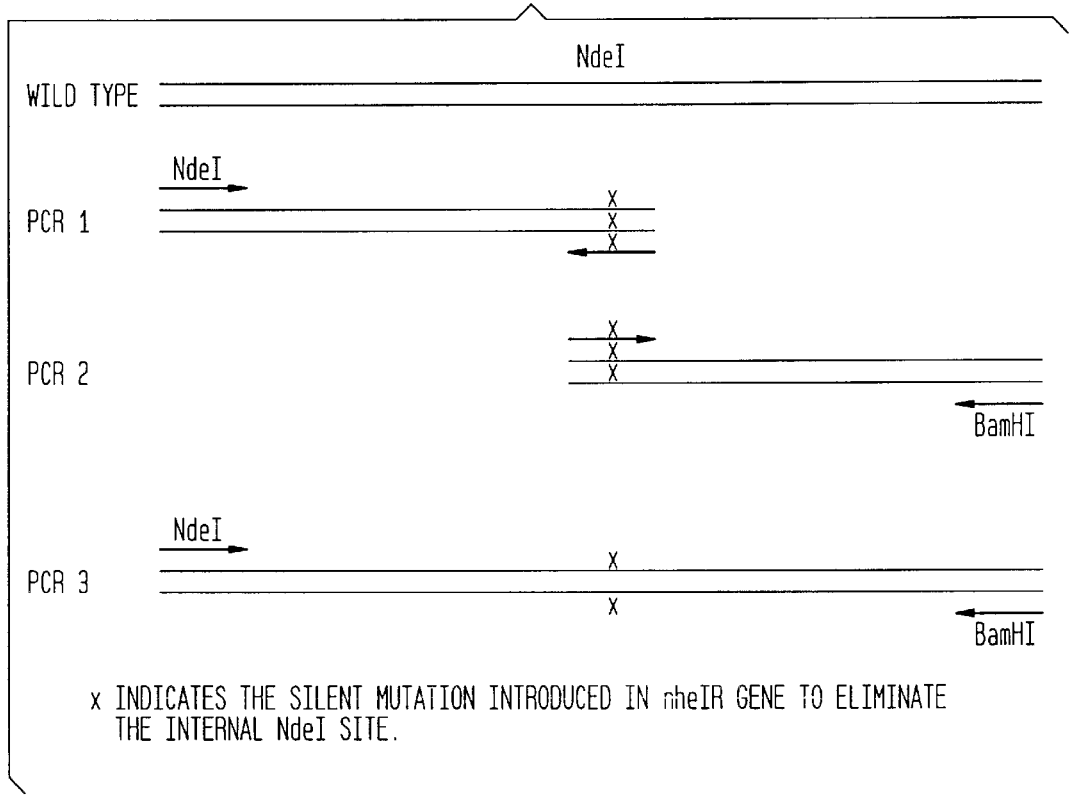
FIG. 4. Schematic diagram of PCR mutagenesis to introduce a silent mutation to remove the internal NdeI site.
Figure 5:
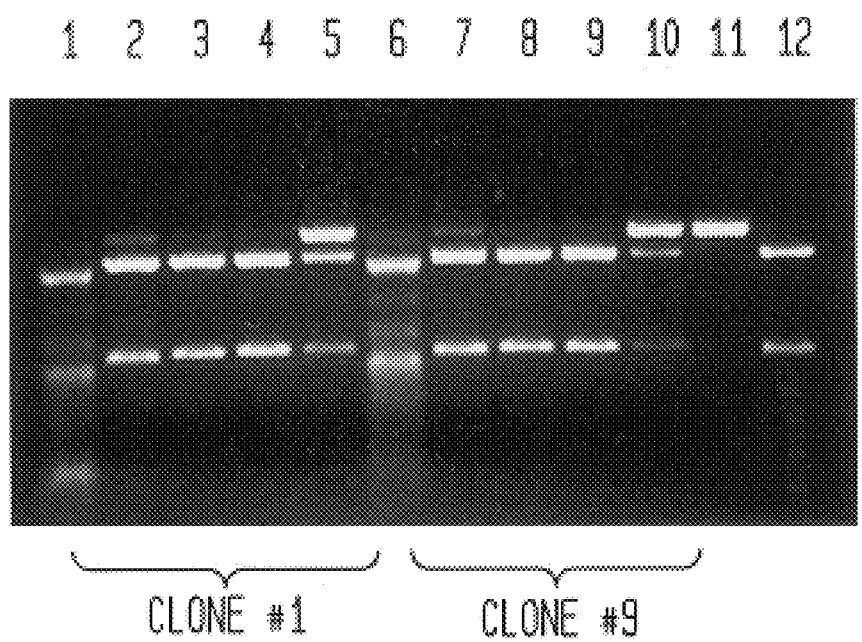
FIG. 5. Restriction digestion using *E. coli* cell extract containing recombinant NheI restriction endonuclease. AvaI-linearized pBR322 was used as the substrate for NheI activity assay. Lanes 1–5, serial dilution of clone #1 cell extract; lanes 6–10, serial dilution of clone #9 cell extract; lane 11, AvaI-linearized pBR322; lane 12, AvaI and NheI double digestion of pBR322. The pBR322 was cleaved into two fragments with 1196 bp and 3165 bp in size respectively. Lanes 1 and 6, 10-fold dilution of cell extract; lanes 2 and 7, 100-fold dilution; lanes 3 and 8, $10^3$-fold dilution; lanes 4 and 9, $10^4$-fold dilution; lanes 5 and 10, $10^5$-fold dilution.

10. Introduction of a Silent Mutation in the nheIR Gene to Eliminate the NdeI Site and Cloning of nheIR Gene in pAII17 by NdeI and BamHI Fragment Insertion In order to remove the NdeI site within the nheIR gene, a silent mutation is introduced into the PCR primers. PCR mutagenesis is performed in PCR reactions 1, 2, and 3 as diagrammed in FIG. 4. The PCR product in reaction 3 is digested with NdeI and BamHI. The NdeI digestion destroys any surviving wild type sequences with the internal NdeI site and enriches the PCR products with the silent mutation. The NdeI-BamHI fragment containing the nheIR gene is ligated to the T7 expression vector pAII17 with compatabel ends and transformed into premodified host ER2566 [pACYC-NheIM]. Transformants are screened for nheIR gene insert. *E. coli* strain ER2566 [pACYC-NheIM, pAII17-NheIR2] is induced with IPTG for 3 h at 37° C. Cells extracts are prepared and assayed for NheI activity. It produces $10^7$ units of recombinant NheI per gram of wet cells, which is approximately 100-fold higher than the native source. The recombinant NheI activity assay in two cell extracts is shown in FIG. 5.

The invention is further illustrated by the following Examples. These Examples are provided to aid in the understanding of the invention and are not construed as a limitation thereof.

The references cited above and below are herein incorporated by reference.

EXAMPLE 1

Cloning of NheI Restriction-modification System in E. coli

1. Preparation of Genomic DNA

Genomic DNA was prepared from *Neisseria mucosa heidelbergensis* (ATCC 25999) by the standard procedure with the following steps: 1. cell lysis with lysozyme, Triton X-100, and SDS; 2. phenol-CHCl$_3$ and CHCl$_3$ extractions; 3. ethanol precipitation; 4. dialysis in TE buffer (change buffer 4 times); 5. RNase A treatment; 6. ethanol precipitation and resuspension of genomic DNA in TE buffer.

2. Construction of an ApoI Partial Genomic DNA Library Using a pRRS Vector

Five μg of *N. mucosa heidelbergensis* genomic DNA was digested with 1 and 0.5 units of ApoI at 50° C. for 30 min. The ApoI partially digested genomic DNA in the range of 2–10 kb was gel-purified. The ApoI partially digested genomic DNA was ligated into EcoRI cut and CIP treated vector pRRS at 16° C. overnight. After the ligation reaction, the ligase was inactivated at 65° C. for 30 min. The ligated DNA was dialyzed by drop dialysis on a membrane on top of 2 liters of sdH$_2$O. The DNA was transferred into RR1 (TonA$^-$, DnaseI$^-$) competent cells by electroporation. Transformants were plated on LB agar plus Amp (100 μg/ml). About 10,000 colonies were obtained in the electroporation. All the transformants were pooled and inoculated into 1 liter of LB broth plus Amp and incubated at 37° C. overnight. Plasmid DNA was prepared from the overnight cells by a Qiagen Mega-prep column.

3. Challenging the ApoI Partial Library DNA with BfaI Digestion and Screening NheI Resistant Clones BfaI recognition sequence C/TAG is the internal 4 bp of NheI recognition sequence G/CTAGC. It was reckoned that cloning and expression of NheI methylase may confer resistance to BfaI digestion. Noncognate methylase modifications sometimes can block overlapping restriction sites. 1–5 μg of the library DNA were digested with BfaI overnight. The BfaI challenged DNA was used to transform RR1 competent cells. Ap$^R$ survivors were screened for resistance to NheI digestion. After screening and digestion of 8 DNA samples, no NheI resistant clones were found.

4. Construction of a New Cloning Vector with Two NheI Sites

Plasmid vector pRRS does not contain any NheI sites. In order to clone NheI methylase gene by the methylase seletion method, two NheI linkers were inserted into SspI and HincII sites in pRRS. The resulting plasmid was named pRRS10. Plasmid pRRS10 was prepared by Qiagen spin columns and digested with EcoRI and treated with CIP. The EcoRI-digested DNA was purified through a low melting agarose gel. Following β-agarase treatment, the DNA was precipitated by ethanol and salt. The DNA pellet was resuspended in TE buffer.

5. Construction of ApoI Partial DNA Library Using pRRS10

The gel-purified ApoI partial DNA fragments were ligated into EcoRI-digested and CIP-treated pRRS10. The ligated DNA was transferred into *E. coli* RR1 competent cells by electroporation. More than 10,000 Ap$^R$ transformants were pooled and amplified in 1 liter overnight cell culture. Primary plasmid DNA library was prepared from the cells and challenged with NheI at 37° C. for 3 h. The challenged DNA was used for transformation into RR1 cells. About 110 Ap$^R$ survivors were found. The transformants were individually cultured overnight and plasmid DNA was prepared by Qiagen spin columns. The plasmid DNA was digested with NheI to check any resistance. Ten plasmid isolates were resistant to NheI digestion among 36 screened. Resistance to NheI digestion could be due to loss of NheI sites in the vector pRRS10 or modification of NheI sites by NheI methylase.

6. DNA Sequencing of the Resistant Clones

Restriction mapping indicated that one resistant clone #22 contains an insert of about 2.8–3 kb. The universal forward and reverse primers of pUC19 were used to sequence the insert. An NheI site was found inserted in the previous HincII site at the multiple cloning sites, indicating the resistance was caused by methylase modification and not due to the loss of NheI site. N4 methylase motifs were also found in the amino acid sequence predicted from the DNA sequence. Three ApoI fragments were gel-purified from resistant clone #22 and subcloned into pUC19. The entire insert was sequenced by primer walking and subcloning. The nheIM gene is 882 bp, encoding a 293-aa protein with predicted molecular mass of 33,268 daltons.

7. Cloning of NheI Restriction Endonuclease Gene (nheIR)

There is one gene downstream of nheIM gene that has 43% identity to a 20 kDa hypothetical protein (O47152) of *E. coli*. Upstream of nheIM gene there is one partial open reading frame (orf) that does not show any homology to known genes in GenBank. Since restriction endonucleases usually are not homologous to each other (except among some isoschizomers), it was concluded that the upstream orf is most likely the nheIR gene. Efforts were made to obtain the upstream coding DNA sequence by inverse PCR amplification. *N. mucosa heidelbergensis* genomic DNA was digested with AluI, HaeII, HhaI, NheI, NlaIII, NspI, SphI, SspI, StyI, TaqI, and TfiI, respectively. The digested DNA was self-ligated at a low DNA concentration at 16° C. overnight. After ligation the ligase was inactivated by heating at 65° C. for 30 min and the DNA was precipitated by ethanol. The circular DNA was then used for inverse PCR amplification of nheIR gene. Two primers were synthesized with the following sequence:

5' gaaaaatagaacatatgatgttgt 3' (214-141) (SEQ ID NO:5)
5' acctttaatggtttatcgtgaatt 3' (214-142) (SEQ ID NO:6)

Inverse PCR was performed using primers 214-141, 214-142, self-ligated DNA template, dNTP, and Taq DNA polymerase plus Vent DNA polymerase (50:1 ratio). Inverse PCR conditions were 95° C. for 1 min, 55° C. for 1 min, and 72° C. for 2 min for 30–35 cycles. Inverse PCR products were found in AluI, NlaIII, NspI, StyI, and TaqI digested/self-ligated DNA samples. The inverse PCR products were gel-purified and sequenced using primers 214-141 and 214-142. After first round of inverse PCR, 339-bp new sequence was obtained. A second round of inverse PCR was performed to amplify more of the upstream sequence. *N. mucosa heidelbergensis* genomic DNA was digested with ApoI, AseI, BssSI, BstUI, HaeIII, HinfI, MseI, NdeI, RsaI, SphI, SspI, TaqI, TfiI, TspRI, and XbaI, respectively. The following primers were synthesized:

5' tacacaaagattagatcctctaat 3' (216-100) (SEQ ID NO:7)
5' gcagcatctctaacaagccatgca 3' (216-101) (SEQ ID NO:8)

Inverse PCR was performed using primers 216-100, 216-101, self-ligated DNA template, dNTP, and Taq DNA polymerase plus Vent DNA polymerase (50:1 ratio). Inverse PCR conditions were 95° C. for 1 min, 55° C. for 1 min, and 72° C. for 2 min for 35 cycles. Inverse PCR products were found in ApoI, AseI, RsaI, SspI, and TaqI digested/self-ligated DNA. The PCR products were gel-purified through low-melting agrose gels and sequenced directly using primers 216-100 and 216-101. An additional 329 bp of new sequence were derived. One open reading frame of 987 bp was found upstream of nheIM gene. This orf is designated as nheIR gene, which encodes a 328-aa protein with predicted molecular mass of 38,197 daltons.

8. Expression of nheIM Gene in *E. coli*

Two primers were synthesized to amplify nheIM gene in PCR. BamHI and SphI sites were engineered into the forward and reverse primers. The primer sequences are:

5' gttggatccggaggtaaataaatgaaattatggaatattattaatgat gat 3' (217-138) (SEQ ID NO:9)

5' aacggcgcatgctcaatcaagcaaccgcgtgcgtgc 3' (217-123). (SEQ ID NO:10)

The nheIM gene was amplified in PCR using 217-138 and 217-123, DNTP, and Taq DNA polymerase plus Vent DNA polymerase (50:1 ratio). Inverse PCR conditions were 95° C. for 1 min, 60° C. for 1 min, and 72° C. for 1.5 min for 25 cycles.

Following digestion with BanHI and SphI, the PCR product was ligated into pACYC184 with compatible ends. The ligated DNA was transformed into ER2683 competent cells. Plasmids with nheIM gene inserts were screened for resistance to NheI digestion. Eleven clones out of 18 were resistant to NheI digestion, indicating efficient M.NheI expression in *E. coli* cells and NheI site modification on the expression plasmid. The host cell ER2683 [pACYC-NheIM] was used for expression of nheIR gene (see section 9).

9. Expression of nheIR Gene in *E. coli* Using a High Copy Plasmid pUC19lacI$^q$ An EcoRI fragment containing the lacI$^q$ gene was gel-purified and ligated into EcoRI site of pUC19 to generate expression plasmid pUC19lacI$^q$. The lacI$^q$ gene encodes Lac repressor which can regulate NheI expression from the lac promoter.

Two primers were synthesized with the following sequence:

5' cgcggatccggaggttaaaaaatgagttcttatcatgatgatttaaat ata 3' (217-139) (11)

5' tccggatcctcataataaaatcctttctaccaacct 3' (217-124) (SEQ ID NO:11)

The nheIR gene was amplified in PCR, using 217-139 and 217-124 primers, dNTP, and Taq DNA polymerase plus Vent DNA polymerase (50:1 ratio). Inverse PCR conditions were 95° C. for 1 min, 60° C. for 1 min, and 72° C. for 1.5 min for 20 cycles. The PCR products were digested with BamHI and purified through a Qiagen spin column. The PCR DNA was ligated into pUC19lacIq$^q$ (BamHI digested and CIP treated). After transformation of the ligated DNA into ER2683 [pACYC-NheIM], transformants were screened for the endonuclease gene insert. Four clones out of 36 contained nheIR gene insert. These four clones (#2, #11, #12, and #30) were induced with IPTG and cell extracts were prepared and assayed for NheI endonuclease activity. #12 clone produces approximately 10,000 units of NheI per gram of wet cells. The remaining three clones produced less NheI activity. The native NheI producing strain *N. mucosa heidelbergensis* (ATCC 25999) produces about 100,000 units of NheI per gram of wet cells. So the NheI yield in the first recombinant strain is about 10-fold lower than the native strain. To increase NheI expression level, nheIR gene was cloned into a T7 expression vector (see section 10).

10. Expression of nheIR Gene in a T7 Expression Vector pAII17

The T7 expression vector pAII17 uses NdeI and BamHI sites for insertion of target gene into the vector. There is a ribosome-binding site upstream of the NdeI site. The start codon (ATG) of the gene to be expressed is fused to the NdeI site (CAT ATG). There is one NdeI site within the nheIR gene so NdeI digestion would disrupt the endonuclease gene. Therefore the NdeI site cannot be used for cloning into pAII17. To solve this problem, BamHI sites were engineered in the forward and reverse primers. A ribosome binding site GGAGGT was also included in the forward primer (see primer 217-139). The nheIR gene was amplified in PCR, digested with BamHI and ligated to BamHI-digested and CIP-treated pAII17 vector. The ligated DNA was transformed into competent cells ER2683 [pACYC-NheIM]. Three clones (#9, #19, and #30) out of 36 contained the nheIR gene insert. Cells ER2683 [pACYC-NheIM, pAII17-NheIR1] were induced with IPTG and cell extracts were prepared to assay NheI activity. The T7 expression strains #9 and #19 produced approximately 100,000 units of NheI, which is about the same level as that produced in the native strain *N. mucosa heidelbergensis*. Further overexpression work was needed to improve the NheI yield.

11. Introduction of a Silent Mutation in the nheIR Gene to Eliminate the NdeI Site and Cloning of nheIR Gene in pAII17 by NdeI and BamHI Fragment Insertion In order to remove the NdeI site within the nheIR gene, silent mutation was introduced into the PCR primers. PCR mutagenesis was performed as diagrammed in FIG. 4.

The following primers were used in three PCR reactions to eliminate the internal NdeI site.

PCR Reaction 1

Forward primer: 5' tatgaggttcatatgagttcttatcatgatgattta aat 3' (225-80) (SEQ ID NO:13) (NdeI site=cat atg, a new NdeI site was engineered at the beginning of the gene).

Reverse mutagenic primer: 5' ttcagctacaacatcgtatgt tctatt 3' (225-82) (SEQ ID NO:14) (The internal wild type sequence catatg is changed to cgtatg, thus removing the internal NdeI site).

PCR Reaction 2

Forward mutagenic primer: 5' aatagaacatacgatgttgtagct gaa 3' (225-81) (SEQ ID NO:15) (the internal sequence catatg is changed to catacg, thus removing the internal NdeI site).

Reverse primer: 5' tccggatcctcataataaaatcctttctaccaa cct 3' (217-124) (SEQ ID NO:16) (gga tcc=BamHI site).

PCR Reaction 3

Templates=PCR products from reactions 1 and 2.
Forward primer=225-80.
Reverse primer=217-124.

The PCR product in reaction 3 was digested with NdeI and BamHI. The NdeI digestion destroyed any surviving wild type sequences with the internal NdeI site and enriched the PCR products with the silent mutation. The NdeI-BamHI fragment containing the nheIR gene was ligated to the T7 expression vector pAII17 with compatible ends and transformed into premodified host ER2566 [pACYC-NheIM]. Transformants were screened for nheIR gene insert. *E. coli* strain ER2566 [pACYC-NheIM, pAII17-NheIR2] was induced with IPTG for 3 h at 37° C. Cell extracts from two clones #1 and #9 were prepared and assayed for NheI activity. It produces $10^7$ units of recombinant NheI per gram of wet cells, which is approximately 100-fold higher than the native source. The recombinant NheI activity assay in cell extracts is shown in FIG. 5. The entire nheIR gene was sequenced using three primers and the C to T silent mutation within the gene was confirmed by sequencing. No other PCR mutations were detected.

The *E. coli* strain ER2566 [pACYC-NheIM, pAII17-NheIR2] has been deposited under the terms and conditions of the Budapest Treaty with the American Type Culture Collection on Oct. 28, 1999 and received ATCC Patent Accession No. PTA-887.

What is claimed is:

1. An isolated DNA coding for the NheI restriction endonuclease, wherein the isolated DNA is obtainable from *Neisseria mucosa heidelbergensis* (ATCC 25999).

2. A recombinant DNA vector comprising a vector into which a DNA segment encoding the NheI restriction endonuclease has been inserted.

3. Isolated DNA encoding the NheI restriction endonuclease and methylase, wherein the isolated DNA is obtainable from ATCC No. PTA-887.

4. A cloning vector which comprises the isolated DNA of claim 3.

5. A host cell transformed by the vector of claim 2.

6. A method of producing recombinant NheI restriction endonuclease comprising culturing a host cell transformed with the vector of claims 2 or 4 under conditions suitable for expression of said endonuclease.

* * * * *

UNITED STATES PATENT AND TRADEMARK OFFICE
CERTIFICATE OF CORRECTION

PATENT NO. : 6,387,681 B1
DATED : May 14, 2002
INVENTOR(S) : Xu et al.

It is certified that error appears in the above-identified patent and that said Letters Patent is hereby corrected as shown below:

Column 1,
Line 10, replace "Nisseria" with -- Neisseria --

Column 2,
Line 50, replace "(1996)" with -- (1996)) --
Line 60, replace "Nisseria" with -- Neisseria --
Lines 64-65, replace "skolund, Gene 88:1-15 (1990)" with -- (Skolund, Gene 88:1-5 (1990)) --

Column 3,
Line 25, replace "doe" with -- does --

Column 6,
Line 10, replace "BaffEI" with -- BamHI --
Line 56, replace "compatabel" with -- compatible --

Column 9,
Line 6, replace "agrose" with -- agarose --
Line 21, replace "DNTP" with -- dNTP --
Line 25, replace "BanHI" with -- BamHI --
Line 44, replace "(11)" with -- (SEQ ID NO:11) --
Line 46, replace "(SEQ ID NO:11)" with -- (SEQ ID NO:12) --

Signed and Sealed this

First Day of October, 2002

Attest:

JAMES E. ROGAN
Attesting Officer   Director of the United States Patent and Trademark Office